(12) United States Patent
Cunningham (10) Patent No.: US 8,142,473 B2
(45) Date of Patent: Mar. 27, 2012

(54) METHOD OF TRANSFERRING ROTATIONAL MOTION IN AN ARTICULATING SURGICAL INSTRUMENT

(75) Inventor: James S. Cunningham, Boulder, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 728 days.

(21) Appl. No.: 12/244,873

(22) Filed: Oct. 3, 2008

(65) Prior Publication Data
US 2010/0087818 A1    Apr. 8, 2010

(51) Int. Cl.
*A61B 17/00* (2006.01)
(52) U.S. Cl. ...................................... 606/205
(58) Field of Classification Search .................. None
See application file for complete search history.

(56) References Cited

U.S. PATENT DOCUMENTS

| | | | |
|---|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,279,753 A | 4/1942 | Knopp |
| 2,305,156 A | 12/1942 | Grubel |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |

(Continued)

FOREIGN PATENT DOCUMENTS

CA       2104423       2/1994

(Continued)

OTHER PUBLICATIONS

European Search Report for EP 11 25 0257 dated Jun. 15, 2011.

(Continued)

*Primary Examiner* — Gary Jackson
*Assistant Examiner* — Amy Shipley (57) ABSTRACT

An endoscopic surgical instrument includes an elongated shaft, which may be articulated to facilitate positioning of an end effector. The instrument accommodates reactionary forces associated with closing the end effector without substantial disruption to the position of the end effector. The instrument includes an elongated shaft housing generally defining distal and proximal shaft axes, and a torsion member extending through the shaft housing. The torsion member transmits rotational displacement from a handle portion of the instrument to the end effector to selectively move the end effector between open and closed configurations. The torsion member comprises a flexible shaft exhibiting a plurality of generally radial slots spaced longitudinally along a length of the flexible shaft.

11 Claims, 4 Drawing Sheets

U.S. PATENT DOCUMENTS

| | | |
|---|---|---|
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,473,077 A | 9/1984 | Noiles et al. |
| 4,485,817 A | 12/1984 | Swigget |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,271,543 A | 12/1993 | Grant et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,888 A | 1/1995 | Zvenyatsky et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,180 A | 2/1995 | Tovey et al. |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |

| | | | | | |
|---|---|---|---|---|---|
| 5,423,810 A | 6/1995 | Goble et al. | 5,611,808 A | 3/1997 | Hossain et al. |
| 5,425,690 A | 6/1995 | Chang | 5,611,813 A | 3/1997 | Lichtman |
| 5,425,739 A | 6/1995 | Jessen | 5,620,415 A | 4/1997 | Lucey et al. |
| 5,429,616 A | 7/1995 | Schaffer | 5,620,453 A | 4/1997 | Nallakrishnan |
| 5,431,672 A | 7/1995 | Cote et al. | 5,620,459 A | 4/1997 | Lichtman |
| 5,431,674 A | 7/1995 | Basile et al. | 5,624,379 A | 4/1997 | Ganz et al. |
| 5,437,292 A | 8/1995 | Kipshidze et al. | 5,624,452 A | 4/1997 | Yates |
| 5,438,302 A | 8/1995 | Goble | 5,626,578 A | 5/1997 | Tihon |
| 5,439,478 A | 8/1995 | Palmer | 5,626,609 A | 5/1997 | Zvenyatsky et al. |
| 5,441,517 A | 8/1995 | Kensey et al. | 5,630,833 A | 5/1997 | Katsaros et al. |
| 5,443,463 A | 8/1995 | Stern et al. | 5,637,110 A | 6/1997 | Pennybacker et al. |
| 5,443,464 A | 8/1995 | Russell et al. | 5,638,003 A | 6/1997 | Hall |
| 5,443,480 A | 8/1995 | Jacobs et al. | 5,643,294 A | 7/1997 | Tovey et al. |
| 5,445,638 A | 8/1995 | Rydell et al. | 5,647,869 A | 7/1997 | Goble et al. |
| 5,445,658 A | 8/1995 | Durrfeld et al. | 5,647,871 A | 7/1997 | Levine et al. |
| 5,449,480 A | 9/1995 | Kuriya | 5,649,959 A | 7/1997 | Hannam et al. |
| 5,451,224 A | 9/1995 | Goble et al. | 5,655,650 A | 8/1997 | Naitou |
| 5,454,823 A | 10/1995 | Richardson et al. | 5,658,281 A | 8/1997 | Heard |
| 5,454,827 A | 10/1995 | Aust et al. | D384,413 S | 9/1997 | Zlock et al. |
| 5,456,684 A | 10/1995 | Schmidt et al. | 5,662,667 A | 9/1997 | Knodel |
| 5,458,598 A | 10/1995 | Feinberg et al. | 5,665,100 A | 9/1997 | Yoon |
| 5,460,629 A | 10/1995 | Shlain et al. | 5,667,526 A | 9/1997 | Levin |
| 5,461,765 A | 10/1995 | Linden et al. | 5,674,220 A | 10/1997 | Fox et al. |
| 5,462,546 A | 10/1995 | Rydell | 5,674,229 A | 10/1997 | Tovey et al. |
| 5,472,442 A | 12/1995 | Klicek | 5,681,282 A | 10/1997 | Eggers et al. |
| 5,472,443 A | 12/1995 | Cordis et al. | 5,688,270 A | 11/1997 | Yates et al. |
| 5,478,351 A | 12/1995 | Meade et al. | 5,690,652 A | 11/1997 | Wurster et al. |
| 5,480,406 A | 1/1996 | Nolan et al. | 5,690,653 A | 11/1997 | Richardson et al. |
| 5,480,409 A | 1/1996 | Riza | 5,690,660 A | 11/1997 | Kauker et al. |
| 5,484,436 A | 1/1996 | Eggers et al. | 5,693,051 A | 12/1997 | Schulze et al. |
| 5,490,819 A | 2/1996 | Nicholas et al. | 5,693,920 A | 12/1997 | Maeda |
| 5,496,312 A | 3/1996 | Klicek | 5,695,522 A | 12/1997 | LeMaire, III et al. |
| 5,496,317 A | 3/1996 | Goble et al. | 5,700,261 A | 12/1997 | Brinkerhoff |
| 5,496,333 A * | 3/1996 | Sackier et al. ............... 606/142 | 5,700,270 A | 12/1997 | Peyser et al. |
| 5,496,347 A | 3/1996 | Hashiguchi et al. | 5,702,390 A | 12/1997 | Austin et al. |
| 5,499,997 A | 3/1996 | Sharpe et al. | 5,707,369 A | 1/1998 | Vaitekunas et al. |
| 5,509,922 A | 4/1996 | Aranyi et al. | 5,709,680 A | 1/1998 | Yates et al. |
| 5,512,721 A | 4/1996 | Young et al. | 5,716,366 A | 2/1998 | Yates |
| 5,514,134 A | 5/1996 | Rydell et al. | 5,720,744 A | 2/1998 | Eggleston et al. |
| 5,520,678 A | 5/1996 | Heckele et al. | 5,722,421 A | 3/1998 | Francese et al. |
| 5,527,313 A | 6/1996 | Scott et al. | 5,725,536 A | 3/1998 | Oberlin et al. |
| 5,528,833 A | 6/1996 | Sakuma | 5,727,428 A | 3/1998 | LeMaire, III et al. |
| 5,529,067 A | 6/1996 | Larsen et al. | 5,735,848 A | 4/1998 | Yates et al. |
| 5,531,744 A | 7/1996 | Nardella et al. | 5,743,906 A | 4/1998 | Parins et al. |
| 5,536,251 A | 7/1996 | Evard et al. | 5,752,973 A | 5/1998 | Kieturakis |
| 5,540,684 A | 7/1996 | Hassler, Jr. | 5,755,717 A | 5/1998 | Yates et al. |
| 5,540,685 A | 7/1996 | Parins et al. | 5,759,188 A | 6/1998 | Yoon |
| 5,540,706 A | 7/1996 | Aust et al. | 5,766,130 A | 6/1998 | Selmonosky |
| 5,540,715 A | 7/1996 | Katsaros et al. | 5,766,166 A | 6/1998 | Hooven |
| 5,542,945 A | 8/1996 | Fritzsch | 5,766,170 A | 6/1998 | Eggers |
| 5,549,637 A | 8/1996 | Crainich | 5,766,196 A | 6/1998 | Griffiths |
| 5,558,671 A | 9/1996 | Yates | 5,766,205 A | 6/1998 | Zvenyatsky et al. |
| 5,558,672 A | 9/1996 | Edwards et al. | 5,769,849 A | 6/1998 | Eggers |
| 5,562,619 A | 10/1996 | Mirarchi et al. | 5,772,655 A | 6/1998 | Bauer et al. |
| 5,562,699 A | 10/1996 | Heimberger et al. | 5,772,670 A | 6/1998 | Brosa |
| 5,562,720 A | 10/1996 | Stern et al. | 5,776,128 A | 7/1998 | Eggers |
| 5,564,615 A | 10/1996 | Bishop et al. | 5,776,130 A | 7/1998 | Buysse et al. |
| 5,569,241 A | 10/1996 | Edwardds | 5,779,646 A | 7/1998 | Koblish et al. |
| 5,569,243 A | 10/1996 | Kortenbach et al. | 5,779,701 A | 7/1998 | McBrayer et al. |
| 5,571,100 A | 11/1996 | Goble et al. | 5,782,834 A | 7/1998 | Lucey et al. |
| 5,573,424 A | 11/1996 | Poppe | H1745 H | 8/1998 | Paraschac |
| 5,573,534 A | 11/1996 | Stone | 5,792,137 A | 8/1998 | Carr et al. |
| 5,573,535 A | 11/1996 | Viklund | 5,792,165 A | 8/1998 | Klieman et al. |
| 5,575,799 A | 11/1996 | Bolanas et al. | 5,792,177 A | 8/1998 | Kaseda |
| 5,575,805 A | 11/1996 | Li | 5,797,537 A | 8/1998 | Oberlin et al. |
| 5,578,052 A | 11/1996 | Koros et al. | 5,797,927 A | 8/1998 | Yoon |
| 5,579,781 A | 12/1996 | Cooke | 5,797,938 A | 8/1998 | Paraschac et al. |
| 5,582,611 A | 12/1996 | Tsukagoshi et al. | 5,797,941 A | 8/1998 | Schulze et al. |
| 5,582,617 A | 12/1996 | Klieman et al. | 5,797,958 A | 8/1998 | Yoon |
| 5,585,896 A | 12/1996 | Yamazaki et al. | 5,800,449 A | 9/1998 | Wales |
| 5,590,570 A | 1/1997 | LeMaire, III et al. | 5,807,393 A | 9/1998 | Williamson, IV et al. |
| 5,591,181 A | 1/1997 | Stone et al. | 5,810,764 A | 9/1998 | Eggers et al. |
| 5,597,107 A | 1/1997 | Knodel et al. | 5,810,805 A | 9/1998 | Sutcu et al. |
| 5,601,224 A | 2/1997 | Bishop et al. | 5,810,808 A | 9/1998 | Eggers |
| 5,601,601 A | 2/1997 | Tal et al. | 5,810,811 A | 9/1998 | Yates et al. |
| 5,601,641 A | 2/1997 | Stephens | 5,810,877 A | 9/1998 | Roth et al. |
| 5,603,711 A | 2/1997 | Parins et al. | 5,814,043 A | 9/1998 | Shapeton |
| 5,603,723 A | 2/1997 | Aranyi et al. | 5,814,054 A | 9/1998 | Kortenbach et al. |
| 5,611,798 A | 3/1997 | Eggers | 5,817,093 A | 10/1998 | Williamsom, IV et al. |

| Patent | Date | Inventor |
|---|---|---|
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,885,288 A | 3/1999 | Aust et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Dafforn et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,399 B1 * | 2/2001 | Palmer et al. ............. 606/205 |
| 6,190,400 B1 | 2/2001 | VanDeMoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,330,502 B1 | 12/2001 | Cetinkunt et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |

| | | | |
|---|---|---|---|
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,491,626 B1 | 12/2002 | Stone et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,723,109 B2 * | 4/2004 | Solingen ............... 606/151 |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,338 B2 | 6/2004 | Hahnen et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,817,974 B2 * | 11/2004 | Cooper et al. ............... 600/142 |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,001 B1 | 8/2005 | Snow |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,008,375 B2 | 3/2006 | Weisel |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,111,769 B2 | 9/2006 | Wales et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |

| | | | |
|---|---|---|---|
| 7,118,587 B2 | 10/2006 | Dycus et al. | |
| 7,131,860 B2 | 11/2006 | Sartor et al. | |
| 7,131,970 B2 | 11/2006 | Moses et al. | |
| 7,131,971 B2 | 11/2006 | Dycus et al. | |
| 7,135,020 B2 | 11/2006 | Lawes et al. | |
| D533,942 S | 12/2006 | Kerr et al. | |
| 7,145,757 B2 | 12/2006 | Shea et al. | |
| 7,147,638 B2 | 12/2006 | Chapman et al. | |
| 7,150,097 B2 | 12/2006 | Sremcich et al. | |
| 7,150,749 B2 | 12/2006 | Dycus et al. | |
| 7,153,314 B2 | 12/2006 | Laufer et al. | |
| D535,027 S | 1/2007 | James et al. | |
| 7,156,842 B2 | 1/2007 | Sartor et al. | |
| 7,156,846 B2 | 1/2007 | Dycus et al. | |
| 7,160,298 B2 | 1/2007 | Lawes et al. | |
| 7,160,299 B2 | 1/2007 | Baily | |
| 7,169,146 B2 | 1/2007 | Truckai et al. | |
| 7,179,255 B2 | 2/2007 | Lettice et al. | |
| 7,179,258 B2 | 2/2007 | Buysse et al. | |
| 7,195,631 B2 | 3/2007 | Dumbauld | |
| D541,418 S | 4/2007 | Schechter et al. | |
| 7,207,990 B2 | 4/2007 | Lands et al. | |
| D541,938 S | 5/2007 | Kerr et al | |
| 7,223,264 B2 | 5/2007 | Daniel et al. | |
| 7,223,265 B2 | 5/2007 | Keppel | |
| 7,232,440 B2 | 6/2007 | Dumbauld et al. | |
| 7,241,288 B2 | 7/2007 | Braun | |
| 7,241,296 B2 | 7/2007 | Buysse et al. | |
| 7,244,257 B2 | 7/2007 | Podjahsky et al. | |
| 7,246,734 B2 | 7/2007 | Shelto, IV | |
| 7,248,944 B2 | 7/2007 | Green | |
| 7,252,667 B2 | 8/2007 | Moses et al. | |
| 7,255,697 B2 | 8/2007 | Dycus et al. | |
| 7,267,677 B2 | 9/2007 | Johnson et al. | |
| 7,270,660 B2 | 9/2007 | Ryan | |
| 7,270,664 B2 | 9/2007 | Johnson et al. | |
| 7,276,068 B2 | 10/2007 | Johnson et al. | |
| 7,300,435 B2 | 11/2007 | Wham et al. | |
| 7,303,107 B2 | 12/2007 | Milliman et al. | |
| 7,303,557 B2 | 12/2007 | Wham et al. | |
| 7,311,709 B2 | 12/2007 | Truckai et al. | |
| 7,314,471 B2 | 1/2008 | Holman | |
| 7,318,823 B2 | 1/2008 | Sharps et al. | |
| 7,329,256 B2 | 2/2008 | Johnson et al. | |
| 7,329,257 B2 | 2/2008 | Kanehira et al. | |
| D564,662 S | 3/2008 | Moses et al. | |
| 7,338,526 B2 | 3/2008 | Steinberg | |
| 7,342,754 B2 | 3/2008 | Fitzgerald et al. | |
| 7,344,268 B2 | 3/2008 | Jhigamian | |
| D567,943 S | 4/2008 | Moses et al. | |
| 7,367,976 B2 | 5/2008 | Lawes et al. | |
| 7,377,920 B2 | 5/2008 | Buysse et al. | |
| 7,384,420 B2 | 6/2008 | Dycus et al. | |
| 7,384,421 B2 | 6/2008 | Hushka | |
| 7,396,336 B2 | 7/2008 | Orszulak et al. | |
| D575,395 S | 8/2008 | Hushka | |
| D575,401 S | 8/2008 | Hixson et al. | |
| 7,435,249 B2 | 10/2008 | Buysse et al. | |
| 7,442,193 B2 | 10/2008 | Shields et al. | |
| 7,442,194 B2 | 10/2008 | Dumbauld et al. | |
| 7,445,621 B2 | 11/2008 | Dumbauld et al. | |
| 7,458,972 B2 | 12/2008 | Keppel | |
| 7,473,253 B2 | 1/2009 | Dycus et al. | |
| 7,476,237 B2 * | 1/2009 | Taniguchi et al. | 606/205 |
| 7,481,810 B2 | 1/2009 | Dumbauld et al. | |
| 7,487,780 B2 | 2/2009 | Hooven | |
| 7,491,201 B2 | 2/2009 | Shields et al. | |
| 7,491,202 B2 | 2/2009 | Odom et al. | |
| 7,500,975 B2 | 3/2009 | Cunningham et al. | |
| 7,510,556 B2 | 3/2009 | Nguyen et al. | |
| 7,513,898 B2 | 4/2009 | Johnson et al. | |
| 7,540,872 B2 | 6/2009 | Schechter et al. | |
| 7,549,995 B2 | 6/2009 | Schultz | |
| 7,553,312 B2 | 6/2009 | Tetzlaff et al. | |
| 7,815,652 B2 * | 10/2010 | Messerly et al. | 606/139 |
| 2002/0013583 A1 | 1/2002 | Camran et al. | |
| 2002/0049442 A1 | 4/2002 | Roberts et al. | |
| 2002/0099372 A1 | 7/2002 | Schulze et al. | |
| 2002/0107517 A1 | 8/2002 | Witt et al. | |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0208186 A1 | 11/2003 | Moreyra |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0143263 A1 | 7/2004 | Schechter et al. |
| 2004/0148035 A1 | 7/2004 | Barrett et al. |
| 2004/0162557 A1 | 8/2004 | Tetzlaff et al. |
| 2004/0193153 A1 | 9/2004 | Sarter et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0273085 A1 | 12/2005 | Hinman |
| 2006/0052778 A1 | 3/2006 | Chapman et al. |
| 2006/0052779 A1 | 3/2006 | Hammill |
| 2006/0064085 A1 | 3/2006 | Schechter |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0111609 A1 | 5/2006 | Bacher |
| 2006/0116675 A1 | 6/2006 | McClurken et al. |
| 2006/0129146 A1 | 6/2006 | Dycus et al. |

| | | |
|---|---|---|
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189981 A1 | 8/2006 | Dycus et al. |
| 2006/0190035 A1 | 8/2006 | Hushka et al. |
| 2006/0206101 A1 | 9/2006 | Lee |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0023477 A1 | 2/2007 | Whitman |
| 2007/0027468 A1 | 2/2007 | Wales |
| 2007/0027469 A1 | 2/2007 | Smith et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0073341 A1 | 3/2007 | Smith |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0175952 A1 | 8/2007 | Shelton |
| 2007/0179476 A1 | 8/2007 | Shelton |
| 2007/0179499 A1 | 8/2007 | Garrison |
| 2007/0198011 A1 | 8/2007 | Sugita |
| 2007/0213712 A1 | 9/2007 | Buysse et al. |
| 2007/0233053 A1 | 10/2007 | Shelton |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0188868 A1 | 8/2008 | Weitzner et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |
| 2010/0030028 A1* | 2/2010 | Cabrera et al. .............. 600/127 |
| 2010/0094289 A1* | 4/2010 | Taylor et al. ................ 606/52 |
| 2010/0274265 A1* | 10/2010 | Wingardner et al. ......... 606/144 |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 | 4/1990 |
| EP | 0467501 | 1/1992 |
| EP | 0518230 | 12/1992 |
| EP | 0541930 | 5/1993 |
| EP | 0572131 | 12/1993 |
| EP | 0584787 | 3/1994 |
| EP | 0589453 | 3/1994 |
| EP | 0589555 | 3/1994 |
| EP | 0623316 | 11/1994 |
| EP | 0624348 | 11/1994 |
| EP | 0650701 | 5/1995 |
| EP | 0694290 | 3/1996 |
| EP | 0717966 | 6/1996 |
| EP | 0754437 | 3/1997 |
| EP | 0517243 | 9/1997 |
| EP | 0853922 | 7/1998 |
| EP | 0875209 | 11/1998 |
| EP | 0878169 | 11/1998 |
| EP | 0887046 | 1/1999 |
| EP | 0923907 | 6/1999 |
| EP | 0986990 | 3/2000 |
| EP | 1034747 | 9/2000 |
| EP | 1034748 | 9/2000 |
| EP | 1025807 | 10/2000 |
| EP | 1034746 | 10/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1159926 | 12/2001 |
| EP | 1177771 | 2/2002 |
| EP | 1301135 | 4/2003 |
| EP | 1330991 | 7/2003 |
| EP | 1486177 | 6/2004 |
| EP | 1472984 | 11/2004 |
| EP | 0774232 | 1/2005 |
| EP | 1527747 | 5/2005 |
| EP | 1530952 | 5/2005 |

| | | |
|---|---|---|
| EP | 1532932 | 5/2005 |
| EP | 1535581 | 6/2005 |
| EP | 1609430 | 12/2005 |
| EP | 1632192 | 3/2006 |
| EP | 1642543 | 4/2006 |
| EP | 1645238 | 4/2006 |
| EP | 1645240 | 4/2006 |
| EP | 1649821 | 4/2006 |
| EP | 1707143 | 10/2006 |
| EP | 1769765 | 4/2007 |
| EP | 1769766 | 4/2007 |
| EP | 1 915 957 A2 | 4/2008 |
| EP | 1 915 966 A1 | 4/2008 |
| EP | 1929970 | 6/2008 |
| EP | 1683496 | 12/2008 |
| EP | 2 044 890 A1 | 4/2009 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000-342599 A2 | 12/2000 |
| JP | 2000-350732 A2 | 12/2000 |
| JP | 2001-008944 A2 | 1/2001 |
| JP | 2001-029356 A2 | 2/2001 |
| JP | 2001-128990 A2 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 | 3/2001 |
| WO | WO 01/54604 | 8/2001 |
| WO | WO 02/07627 | 1/2002 |
| WO | WO 02/34147 A1 | 5/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 2008/042423 A2 | 4/2008 |
| WO | WO 2008/045348 | 4/2008 |
| WO | WO 2008/045350 | 4/2008 |

OTHER PUBLICATIONS

Michael Choti, "Abdominoperineal Resection with the LigaSure Vessel Sealing System and LigaSure Atlas 20 cm Open Instrument" ; Innovations That Work, Jun. 2003.

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With The LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98957771 dated Aug. 9, 2001.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05019429.9 dated May 6, 2008.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008515.6 dated Jan. 8, 2009.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended—EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 014016 dated Jan. 28, 2008.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report EP 07 021646.0 dated Jul. 9, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report PCT/US98/18640 dated Dec. 17, 1998.
Int'l Search Report PCT/US98/23950 dated Dec. 29, 1998.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US03/28534 dated Dec. 19, 2003.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

METHOD OF TRANSFERRING ROTATIONAL MOTION IN AN ARTICULATING SURGICAL INSTRUMENT

BACKGROUND

1. Technical Field

The present disclosure relates generally to an apparatus for remotely actuating an end effector disposed at a distal end of a surgical instrument. In particular, the apparatus transmits a rotational movement through a shaft of the instrument to maintain a position of the end effector throughout actuation of the end effector.

2. Background of Related Art

Typically in a laparoscopic, an endoscopic, or other minimally invasive surgical procedure, a small incision or puncture is made in a patient's body. A cannula is then inserted into a body cavity through the incision, which provides a passageway for inserting various surgical devices such as scissors, dissectors, retractors, or similar instruments. To facilitate operability through the cannula, instruments adapted for laparoscopic surgery typically include a relatively narrow shaft supporting an end effector at its distal end and a handle at its proximal end. Arranging the shaft of such an instrument through the cannula allows a surgeon to manipulate the proximal handle from outside the body to cause the distal end effector to carry out a surgical procedure at a remote internal surgical site. This type of laparoscopic procedure has proven beneficial over traditional open surgery due to reduced trauma, improved healing and other attendant advantages.

An articulating laparoscopic or endoscopic instrument may provide a surgeon with a range of operability suitable for a particular surgical procedure. The instrument may be configured such that the end effector may be aligned with an axis of the instrument to facilitate insertion through a cannula, and thereafter, the end effector may be selectively articulated, pivoted or moved off-axis as necessary to appropriately engage tissue. When the end effector of an articulating instrument includes a pair of jaw members for grasping tissue, a force transmission mechanism such as a flexible control wire may be provided to open or close the jaws. For example, the control wire may extend through an outer shaft from the handle to the jaws such that the surgeon may create a tension in the control wire to cause the jaws to move closer to one another. The closure or clamping force generated in the jaws may be directly related to the tension in the control wire applied by the surgeon.

One type of laparoscopic or endoscopic instrument is intended to generate a significant closure force between jaw members to seal small diameter blood vessels, vascular bundles or any two layers of tissue with the application electrosurgical or RF energy. The two layers may be grasped and clamped together by the jaws of an electrosurgical forceps, and an appropriate amount of electrosurgical energy may be applied through the jaws. In this way, the two layers of tissue may be fused together. The closure forces typically generated by this type of procedure may present difficulties when using a typical control wire to open and close the jaws of an articulating instrument.

For example, a surgeon's efforts to position the jaws may be frustrated by a tendency for a control wire under tension to realign the jaws with the axis of the instrument after the jaws have been articulated off-axis. Although this tendency may be observed in any type of articulating instrument, the tendency is particularly apparent when the closure forces and necessary tension in the control wire are relatively high, as is common in an electrosurgical sealing instrument. This tendency may be created by the direction of reaction forces through the outer shaft of the instrument.

SUMMARY

The present disclosure describes an endoscopic surgical instrument that transmits rotational movement to an end effector through a shaft of the instrument. The instrument includes an elongated shaft housing defining distal and proximal ends. The distal end of the shaft housing generally defines a distal shaft axis and the proximal end of the shaft housing generally defines a proximal shaft axis. A torsion member extends through the shaft housing and includes distal and proximal ends. The distal end of the torsion member is configured for rotational movement in response to rotational movement of the proximal end of the torsion member. An end effector is coupled to the distal end of the shaft housing. The end effector is moveable between open and closed configurations in response to rotational movement of the distal end of the torsion member. A handle is coupled to the proximal end of the shaft housing, and includes an actuation mechanism functional to selectively induce rotational movement at the proximal end of the torsion member. The torsion member includes a flexible shaft exhibiting a plurality of generally radial slots spaced longitudinally along a length of the flexible shaft.

The torsion member may be constructed as an elongated tube defining a lumen therethrough. The elongated tube may be constructed of stainless steel. The plurality of slots may include at least two opposed slots having a radial displacement from one another of about 180 degrees, or the plurality of slots may include at least three slots having a radial displacement from one another of about 120 degrees. The shaft housing may be flexible along a length thereof and may be sufficiently rigid to support the end effector in a position when the shaft housing is in a misaligned configuration.

The end effector may include a pair of opposable jaw members. At least one of the jaw members of the pair of opposable jaw members may be coupled to a source of electrosurgical energy. The end effector may also include an input shaft coupled to the torsion member to receive rotational motion therefrom, and the input shaft may be coupled to a power screw for driving a translation nut longitudinally upon rotational motion in the power screw. The actuation mechanism of the handle may include a nut operatively coupled to a moveable handle such that movement of the movable handle moves the nut longitudinally, and the nut may be coupled to a lead screw such that longitudinal motion of the nut drives rotational motion of the lead screw.

According to another aspect of the disclosure, the torsion member may include a plurality of substantially rigid segments coupled to one another by universal joints or constant velocity joints.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
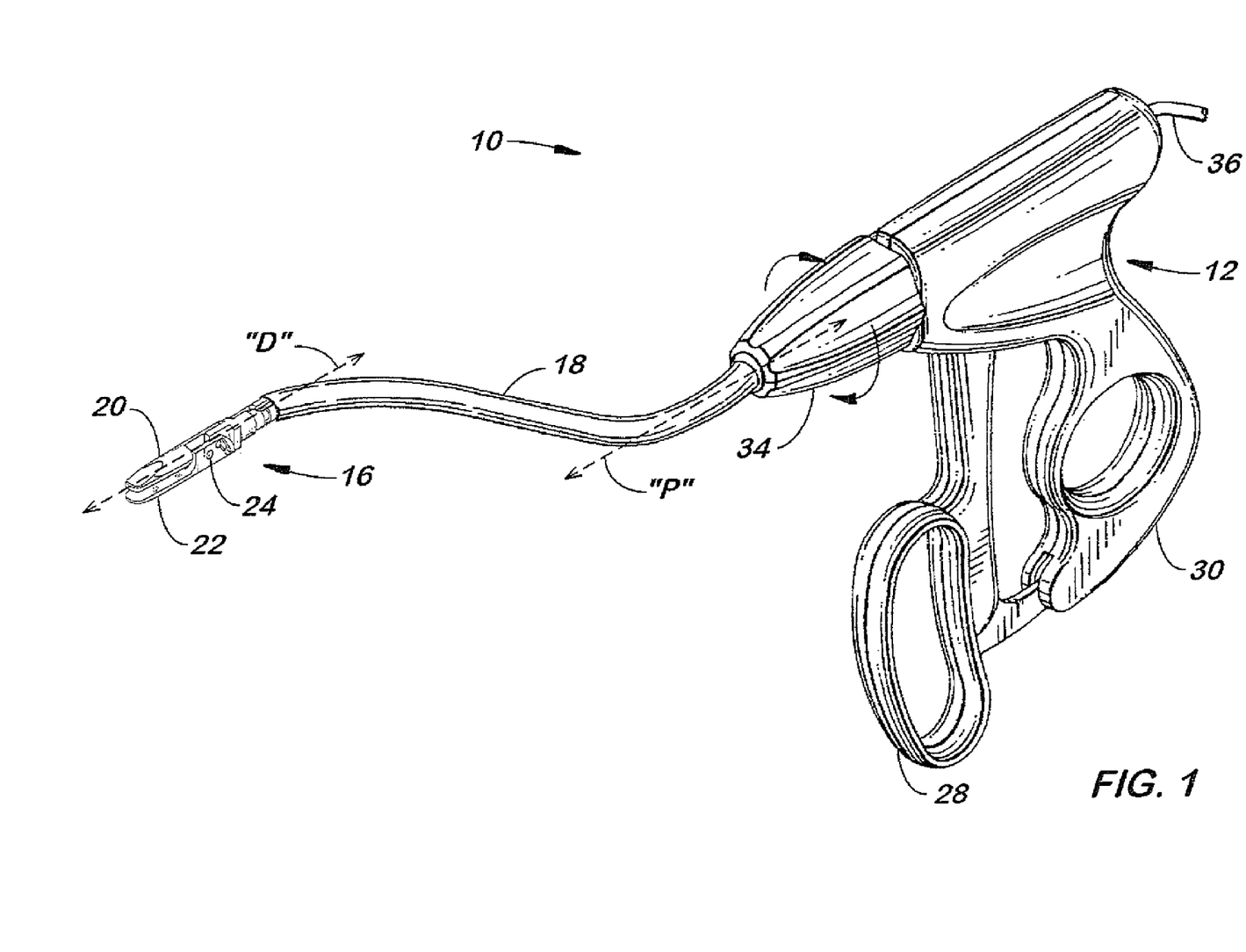
FIG. 1 is a perspective view of an articulating laparoscopic surgical instrument having an end effector in accordance with the present disclosure.

Referring initially to FIG. 1, an articulating endoscopic instrument is depicted generally as 10. The instrument 10 includes a handle portion 12 near a proximal end, an end effector 16 near a distal end and an elongated shaft 18 therebetween. Elongated shaft 18 defines a proximal shaft axis "P" substantially aligned with the handle portion 12 and a distal shaft axis "D" substantially aligned with the end effector 16.

The elongated shaft 18 is flexible such that the proximal shaft axis "P" and the distal shaft axis "D" may be selectively aligned or misaligned as shown. For example, the elongated shaft 18 may be bent in any direction, e.g., in both a horizontal and a vertical plane simultaneously, to assume a compound curve as shown. Other configurations are contemplated for elongated shaft 18, such as hinged or segmented wherein the shaft 18 is constructed from a plurality of substantially rigid members that are nested in series and/or pivotable relative to one another. A degree of rigidity may be maintained by the elongate shaft 18 such that the elongate shaft 18 supports itself to facilitate positioning of the end effector 16 at an anatomical position. Alternatively, a steering and locking mechanism (not shown) may be associated with the end effector 16 such that an operator may position the end effector 16 and lock the orientation of the elongated shaft 18 using a control surface (not shown) on the handle portion 12.

End effector 16 includes a pair of opposing jaw members 20 and 22. The jaw members 20, 22 are operable from the handle portion 12 to move between an open configuration (see FIG. 2A) to receive tissue, and a closed configuration (see FIG. 2B) to clamp the tissue and impart an appropriate clamping force thereto. When the end effector 16 is in the open configuration, a distal portion of each of the jaw members 20, 22 is spaced from the distal portion of the other of the jaw members 20, 22. In contrast, when the end effector 16 is in the closed configuration, the distal portions of the jaw members 20, 22 are closer together.

The motion exhibited by end effector 16 may be described as bilateral movement. Both jaw members 20 and 22 are pivotable about a pivot pin 24 such that each jaw member 20, 22 moves relative to distal shaft axis "D" as the end effector 16 is moved between the open and closed configurations. However, unilateral motion is also contemplated wherein an end effector (not shown) includes a stationary jaw that remains fixed relative to distal shaft axis "D" and a moveable jaw that moves relative to distal shaft axis "D" to move the end effector between the open and closed configurations. Further, non-pivotable motion is contemplated. For example, an end effector (not shown) may include jaw members configured for substantially parallel motion.

End effector 16 is configured for electrosurgical tissue sealing. At least one of the jaw members 20, 22 is connected to a source of electrical energy such that the electrical energy may transmitted through tissue clamped between the jaw members. To form an effective tissue seal, a relatively high clamping force is typically generated to impart a closure pressure on the tissue in the range of from about 3 kg/cm$^2$ to about 16 kg/cm$^2$. As described in greater detail below, instrument 10 is configured to accommodate pressures in this range such that elongate shaft 18 exhibits no substantial tendency to inadvertently realign the proximal shaft axis "P" and the distal shaft axis "D." A more complete description of the tissue sealing generally may be found in U.S. Pat. No. 7,367,976 to Lawes et al.

Handle portion 12 is manipulatable by the surgeon from outside a body cavity to control the movement of the end effector 16 positioned inside the body at a tissue site. For example, the surgeon may separate and approximate a pivoting handle 28 relative to a stationary handle 30 to respectively open and close jaw members 20, 22. Also, a surgeon may adjust an orientation of the jaw members by rotating knob 34. Handle portion 12 accommodates a cable 36 for delivery of an electrosurgical current to the instrument 10.

Figure 2A:
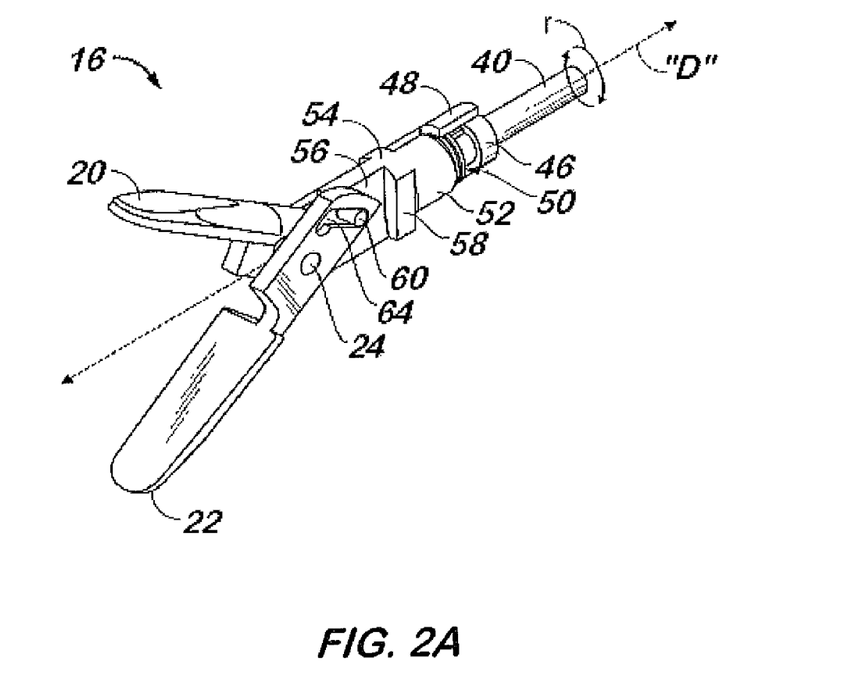
FIG. 2A is a perspective view of the end effector of FIG. 1 in an open configuration.
Figure 2B:
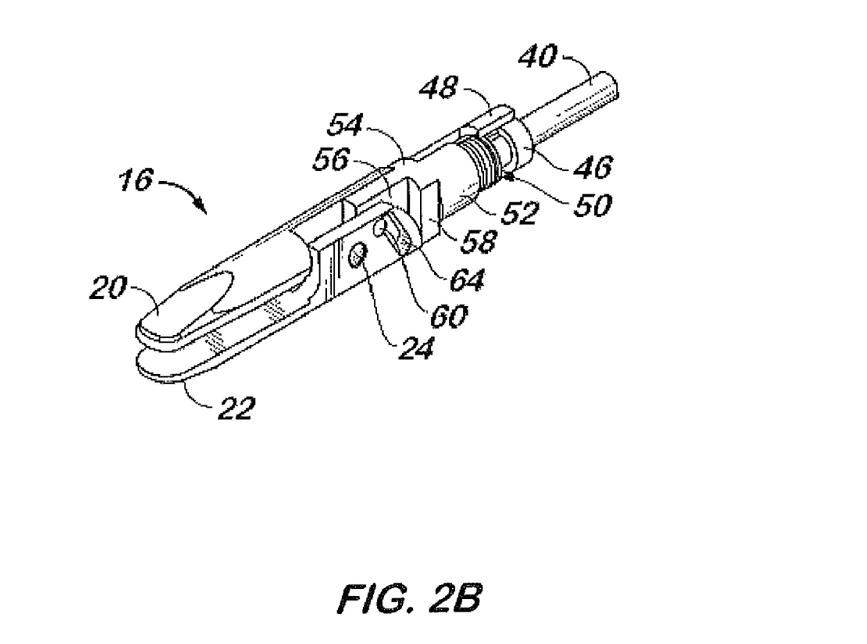
FIG. 2B is a perspective view of the end effector of FIG. 1 in a closed configuration.

Referring now to FIGS. 2A and 2B, end effector 16 is adapted to move between the open configuration depicted in FIG. 2A and the closed configuration depicted in FIG. 2B. This motion of the jaw members 20, 22 is achieved upon the application of a torsion force to end effector 16. Therefore, a control wire placed in tension, which as discussed above may generate reactionary forces in the outer shaft of an instrument and tend to frustrate the articulation of the instrument, is not necessary.

End effector 16 is adapted to receive the torsion force through input shaft 40 such that input shaft 40 may rotate about a distal shaft axis "D" as indicated by arrows "r." Input shaft 40 provides connectivity to a suitable external source of rotational motion (e.g. slotted shaft 44 discussed below). Input shaft 40 rotates inside a fixed bearing member 46. Fixed bearing member 46 provides mounting surfaces for direct or indirect fixed coupling to the distal end of elongated shaft 18, which remains stationary relative thereto. In this way, the entire end effector 16 is supported by the instrument 10 and may be caused to articulate relative to the proximal shaft axis "P" (FIG. 1). Fixed bearing member 46 also supports a reactive member 48 on an outer surface thereof. Reactive member 48 extends distally from fixed bearing member 46 and supports pivot pin 24 extending into jaw members 20 and 22. An additional reactive member (not shown) may be supported by fixed bearing member 46 so as to mirror the reactive member 48 shown and provide additional support to pivot pin 24. Reactive member 48 remains stationary relative to fixed bearing member 46 as jaw members 20, 22 pivot open and closed.

A lead screw or power screw 50 is supported at a distal end of input shaft 40. The power screw 50 is coupled to the input shaft 40 such that both the power screw 50 and the input shaft 40 rotate together. Rotational movement of the power screw 50 drives a translation nut 52 longitudinally along distal shaft axis "D." For example, rotation of power screw 50 in a first direction advances translation nut 52 from the position depicted in FIG. 2A where the translation nut is disposed at a first distance from the fixed bearing member 46, to the position depicted in FIG. 2B where the translation nut 52 is a second distance from the fixed bearing member 46 that is greater than the first distance. Likewise, rotation of power screw 50 in an opposite direction withdraws translation nut 52 such that translation nut 52 becomes closer to the fixed bearing member 46.

A force transfer member 54 is supported at a distal end of translation nut 52. Force transfer member 54 may be coupled to translation nut 52 or may be formed integrally therewith such that the force transfer member 54 translates along with the translation nut 52. Force transfer member 54 is formed with a central web 56 having a pair of proximal flanges 58 extending therefrom in opposite directions. An opposed pair of cam pins 60 protrudes laterally from central web 56 into jaw members 20, 22.

The cam pins 60 work in conjunction with proximal flanges 58 to open and close the jaw members 20, 22. Cain pins 60 engage a pair of cam slots 64 on the jaw members 20, 22 as the cam pins 60 translate distally along with force transfer member 54. Distal translation of cam pins 60 through cam slots 64 cause the jaw members 20, 22 to move from the open configuration of FIG. 2A to a nearly-closed configuration where the cam pins 60 encounter a bend in the cam slots 64. In the nearly-closed configuration, the proximal flanges 58 contact proximal faces of jaw members 20, 22 and a force is transferred from the cam pins 60 to the proximal flanges 130 of the force transfer member 54. Further distal translation of the force transfer member 54 will move the jaws from the nearly-closed configuration to the closed configuration of FIG. 2B.

In the closed configuration of FIG. 2B, the jaw members 20, 22 may generate a significant clamping force that can be directed at tissue positioned between the jaw members 20, 22. As the proximal flanges 130 press distally against the jaw members 20, 22, the jaw members 20, 22 press distally on the pivot pin 24 coupled to the reactive member 48. An opposite reaction force is realized as a tensile force in the reactive member 48, which links the jaw members to the fixed bearing member 46. Because the reaction force is contained entirely within the end effector 16, this arrangement allows instrument 10 (FIG. 1), to which the end effector 16 is attached, to close jaw members 20, 22 without creating a tendency for distal shaft axis "D" to realign itself with the proximal shaft axis "P." This functionality is afforded by an instrument 10 equipped to supply rotational motion to the end effector 16.

Figures 3, 4:
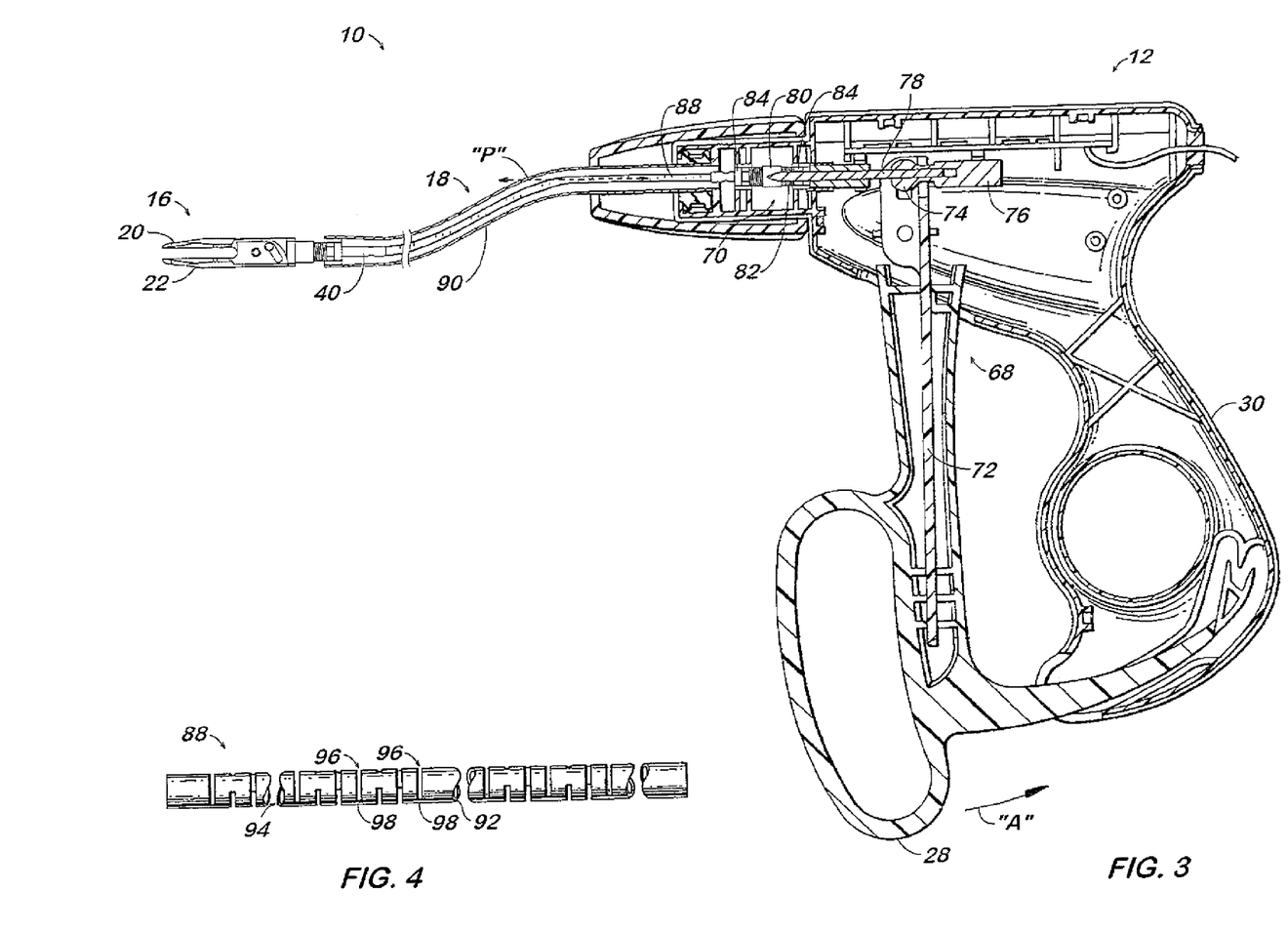
FIG. 3 is a schematic view of the instrument of FIG. 1 depicting a torsion device for transmitting rotational motion to the end effector.
FIG. 4 is a side view of a slotted shaft of the torsion device of FIG. 3.

Referring now to FIG. 3, instrument 10 is depicted schematically with end effector 16 in the closed configuration. Pivoting handle 28 is approximated to stationary handle 30, and distal portions of jaw members 20, 22 are closer together relative to the open configuration depicted in FIG. 2A. An actuation mechanism 68 receives motion from the pivoting handle to prompt the rotational motion allowing jaw members 20, 22 may be remotely controlled from the handle portion 12.

Actuation device 68 includes a motion converter 70 housed in handle portion 12. Motion converter 70 converts longitudinal motion supplied by die movement of pivoting handle 28 into rotational motion. To drive the motion converter 70, pivoting handle 28 is coupled to a flexible arm 72, which engages a rounded head portion 74 of a connector 76. Connector 76 is, in turn, coupled to a piston 78. Approximating pivoting handle 28 to stationary handle 30 in the direction of arrow "A" pivots the flexible arm 72 against the rounded head portion 74. The rounded head portion 74 converts the pivotal motion of the pivoting handle 28 into longitudinal motion which drives the connector 76 and piston 78 in a distal direction. Driving the piston 78 in a distal direction drives a nut 80 distally along a lead screw or power screw 82. The power screw 82 is mounted between bearing members 84 such that the power screw 82 rotates about proximal shaft axis "P" as nut 80 is driven longitudinally.

A torsion member 88 is provided through a shaft housing 90. The shaft housing 90 may be flexible along a length thereof and sufficiently rigid to support the end effector in a position when the flexible shaft is in the misaligned configuration, i.e., when the proximal shaft axis and the distal shaft axis are substantially misaligned. The torsion member 88 is configured to transmit rotational motion from the handle portion 12 to the end effector 16. The torsion member 88 is jointed or flexible to permit shaft 18 to navigate a tortuous path, and exhibits an ability to transmit a rotational displacement along its length. A proximal end of the torsion member 88 is coupled to power screw 82 such that the proximal end of the torsion member 88 rotates with the power screw 82. The distal end of the torsion member 88 is coupled to the input shaft 40 of end effector 16 to supply rotational motion thereto. As described above, rotating input shaft 40 causes the end effector 16 to move to the closed configuration without transferring reactive forces the shaft housing 90 that tend to realign the shaft 18.

In this manner, approximation of pivoting handle 28 with stationary handle 30 results in the end effector 16 moving to the closed configuration. It follows that separation of pivoting handle 28 from stationary handle 30 results in the end effector 16 moving to the open configuration by the reverse process. The reverse process begins as flexible arm 72 drives the connector 76 in a proximal direction, which, in turn, draws the piston 78 in the proximal direction. This draws nut 80 in the proximal direction, which causes power screw 82 to rotate in the opposite direction than when the nut 80 is driven proximally. This motion in the opposite direction is transmitted through torsion member 88 to the input shaft 40, which causes the end effector 16 to move to the open configuration.

Referring now to FIG. 4, torsion member 88 comprises an elongate flexible tube having a generally cylindrical wall 92. A lumen 94 extends through the cylindrical wall for the length of the torsion member 88 to facilitate the passage of electrical wires, fluids or other materials through the shaft 18. The cylindrical wall 92 exhibits a length and thickness that permits the torsion member 88 to transmit torque and rotational movement while remaining flexible to assume the shape imposed upon the shaft 18. Contributing to the flexibility of the shaft is a plurality of slots 96 extending radially though the cylindrical wall 92 to define living hinges 98 opposite the slots 96. Living hinges 98 are portions of the cylindrical wall 92 where the cylindrical wall 92 is weekend in bending to allow the torsion member 88 to pivot, and remains sufficiently strong in torsion to allow the torsion member 88 to transmit radial displacement along its length.

Slots 96 and corresponding living hinges 94 are spaced longitudinally along the torsion member 88. The number of slots 96 and longitudinal spacing between adjacent slots 96 may be selected according to a bend radius to be achieved by the torsion member 88. Slots 96 are also radially offset with respect to one another to allow the torsion member 88 to bend in a plurality of directions. For example, two opposed slots 96 radially offset by about 180 degrees from one another can allow the torsion member to pivot in two directions in a single plane. Similarly, three slots 96 offset by 120 degree increments can allow the torsion member to bend in multiple planes simultaneously. The radial offset between adjacent slots 96 may be selected accommodate a particular shape to be achieved by the torsion member 88.

The cylindrical wall 92 is constructed from stainless steel tube to provide a high degree of torque transmission, but other materials may be selected to provide other characteristics. For example, polymers such as nylon or polyethylene may offer greater flexibility and excellent biocompatibility. Alternate shaft geometries are also contemplated. For example, spiral cut notches or braided wire shafts (not shown) may be included for use in a torsion member. Also a solid shaft, i.e., with no central lumen, may be used.

Figure 5:
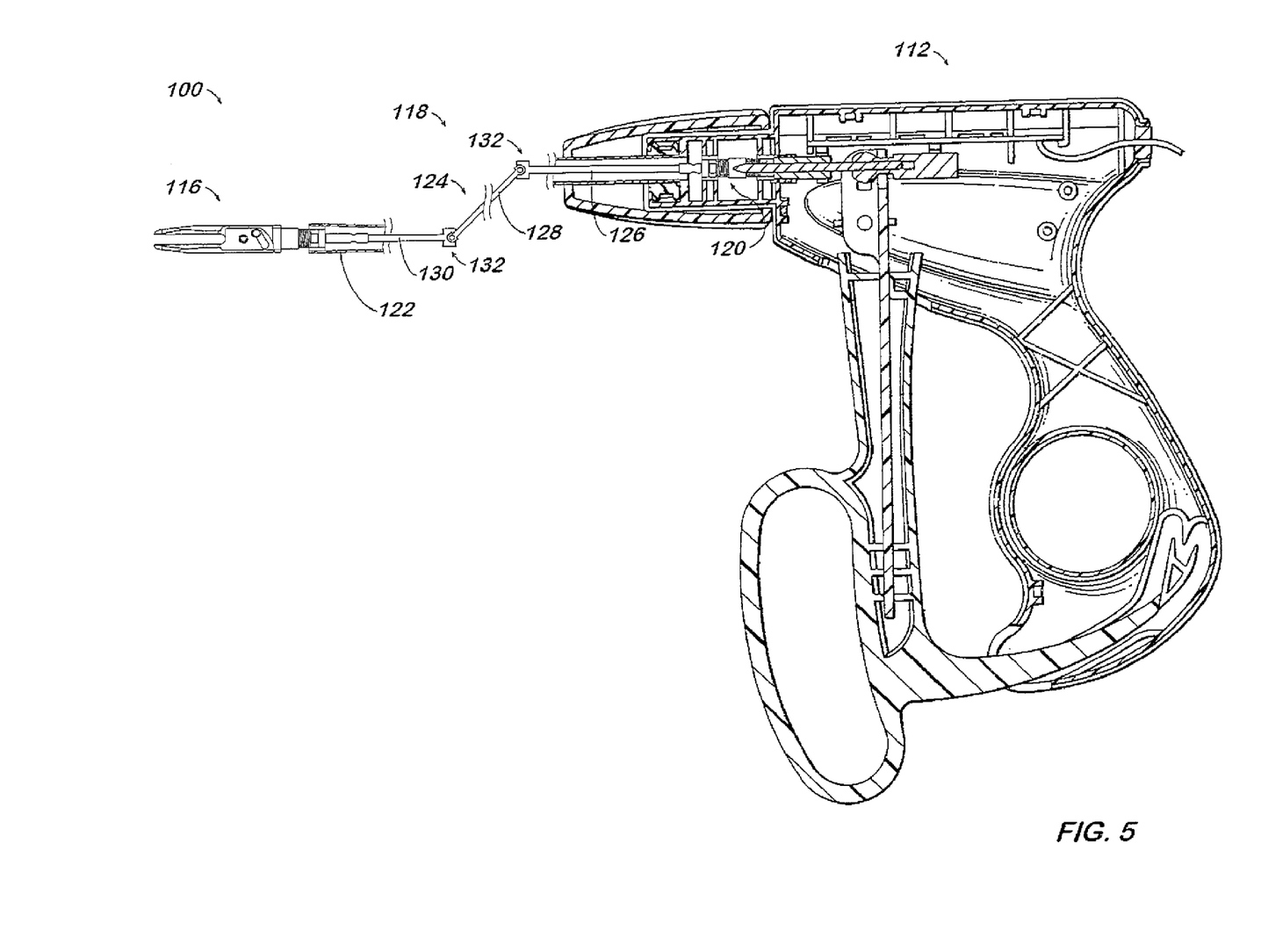
FIG. 5 is a schematic view of an alternate embodiment of a surgical instrument in accordance with the present disclosure.

Referring now to FIG. 5, an alternate embodiment of a surgical instrument is depicted generally as 100. Instrument 100 includes a handle portion 112 and an end effector 116 coupled to one another through an articulating shaft 118. Handle portion 112 and end effector 116 are similar to handle portion 12 and end effector 16 of instrument 10 (see FIG. 3).

The handle portion 112 is equipped with a motion converter 120 to convert longitudinal motion generated by movement of handle portion 112 into rotational motion. Similarly, end effector 116 is configured to receive rotational motion to move between open and closed configurations. Unlike instrument 10, rotational motion is transmitted through a shaft housing 122 through a torsion member 124 comprising a plurality of substantially rigid segments.

Torsion member 124 includes a proximal torsion bar 126 coupled to motion converter 120 at a proximal end and a central torsion bar 128 at a distal end. Likewise, the central torsion bar 128 is coupled to a distal torsion bar 130 opposite the proximal torsion bar 126. The distal torsion bar 130 is coupled to the end effector 116 to provide rotational motion thereto. Each of the torsion bars 126, 128, 130 is elongate and substantially rigid. The torsion bars 126, 128, 130 are each capable of rotation about an independent axis due to their interconnection by joint members 132.

Joint members 132 may include such mechanisms as a universal joints or constant velocity joints. Universal joints typically consist of a pair of hinges oriented 90 degrees from each other located in close proximity to one another. A constant velocity joint may assume different forms, and is similar to a universal joint as this type of joint is commonly used in shafts that transmit rotational motion through angled pathways.

Since the torsion member 124 is coupled directly to the end effector 116 and since the torsion force transmitted through torsion member 124 is axial with the torsion member 124, the reactionary forces associated with moving the end effector 116 to the closed configuration are passed back through the torsion member 124 rather than through a shaft housing 132. In this way, the unintentional realignment of shaft 118 may be avoided.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a shaft housing including distal and proximal ends, the distal end of the shaft housing generally defining a distal shaft axis and the proximal end of the shaft housing generally defining a proximal shaft axis;
   a torsion member extending through the shaft housing and including distal and proximal ends, the distal end of the torsion member configured for rotational movement in response to rotational movement of the proximal end of the torsion member;
   an end effector coupled to the distal end of the shaft housing, the end effector moveable between open and closed configurations in response to rotational movement of the distal end of the torsion member; and
   a handle coupled to the proximal end of the shaft housing, the handle including an actuation mechanism configured to selectively induce rotational movement at the proximal end of the torsion member;
   wherein the torsion member comprises a flexible shaft having a plurality of generally radial slots defined in spaced longitudinal orientation along a length of the flexible shaft.

2. The instrument according to claim 1, wherein the torsion member comprises an elongated tube defining a lumen therethrough.

3. The instrument according to claim 2, wherein the elongated tube is constructed of stainless steel.

4. The instrument according to claim 1, wherein the plurality of slots includes at least two opposed slots radially spaced relative to one another by about 180 degrees.

5. The instrument according to claim 1, wherein the plurality of slots includes at least three slots radially displaced relative to one another by about 120 degrees.

6. The instrument according to claim 1, wherein the shaft housing is flexible along a length thereof and sufficiently rigid to support the end effector in a position when the shaft housing is disposed in a misaligned configuration.

7. The instrument according to claim 1, wherein the end effector includes a pair of opposable jaw members.

8. The instrument according to claim 6, wherein at least one of the jaw members of the pair of opposable jaw members is coupled to a source of electro surgical energy.

9. The instrument according to claim 1, wherein the end effector includes an input shaft coupled to the torsion member configured to receive rotational motion therefrom, and wherein the input shaft is coupled to a power screw that drives a translation nut longitudinally upon rotational motion of the power screw.

10. The instrument according to claim 1, wherein the actuation mechanism of the handle includes a nut operatively coupled to a moveable handle such that movement of the movable handle moves the nut longitudinally, and wherein the nut is coupled to a lead screw such that longitudinal motion of the nut drives rotational motion of the lead screw.

11. A surgical instrument, comprising:
    an elongated shaft housing including distal and proximal ends, the distal end of the shaft housing generally defining a distal shaft axis and the proximal end of the shaft housing generally defining a proximal shaft axis;
    a torsion member extending through the shaft housing and including distal and proximal ends, the distal end of the torsion member configured for rotational movement in response to rotational movement of the proximal end of the torsion member;
    an end effector coupled to the distal end of the shaft housing, the end effector moveable between open and closed configurations in response to rotational movement of the distal end of the torsion member; and
    a handle coupled to the proximal end of the shaft housing, the handle including an actuation mechanism configured to selectively induce rotational movement at the proximal end of the torsion member;
    wherein the torsion member includes a plurality of substantially rigid segments coupled to one another by universal joints or constant velocity joints.

* * * * *